United States Patent
Arjah et al.

(10) Patent No.: US 10,155,707 B2
(45) Date of Patent: Dec. 18, 2018

(54) OLEFIN HYDRATION PROCESS USING OSCILLATORY BAFFLED REACTOR

(71) Applicant: Saudi Arabian Oil Company, Dhahran (SA)

(72) Inventors: Abeer Arjah, Doha (SA); Kareemuddin M. Shaik, Dhahran (SA); Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 311 days.

(21) Appl. No.: 14/879,601

(22) Filed: Oct. 9, 2015

(65) Prior Publication Data

US 2016/0115107 A1    Apr. 28, 2016

Related U.S. Application Data

(63) Continuation-in-part of application No. 14/016,798, filed on Sep. 3, 2013, now Pat. No. 9,187,388.
(Continued)

(51) Int. Cl.
*B01J 19/00* (2006.01)
*B01J 19/18* (2006.01)
(Continued)

(52) U.S. Cl.
CPC .............. *C07C 29/04* (2013.01); *B01J 19/006* (2013.01); *B01J 19/185* (2013.01);
(Continued)

(58) Field of Classification Search
CPC .... B01J 2219/00094; B01J 2219/00108; B01J 2219/0011; B01J 2219/00777;
(Continued)

(56) References Cited

U.S. PATENT DOCUMENTS 2,663,744 A   12/1953   Lukasiewicz et al.
3,440,293 A    4/1969   Rosscup
(Continued)

FOREIGN PATENT DOCUMENTS

CN    1958143 A    5/2007
EP    2208719 A1    7/2010
(Continued)

OTHER PUBLICATIONS

English Translation of JP2007-230937, Sep. 13, 2007, pp. 1-13.*
(Continued)

*Primary Examiner* — Pancham Bakshi
*Assistant Examiner* — Mark R Luderer
(74) *Attorney, Agent, or Firm* — Bracewell LLP; Constance G. Rhebergen; Linda L. Morgan (57) ABSTRACT

A butanol production system and method for producing refined mixed butanols includes an internal baffle single pass reactor having an internal fluid conduit defined by an internal wall. The internal fluid conduit contains a process fluid comprising water, mixed butenes and mixed butanols, to form a crude product. Internal flow baffles are located along a length of the internal fluid conduit. Baffled cells are defined at an outer diameter by the internal wall and at ends by the internal flow baffles. A separation system separates water and mixed butenes from the crude product to produce refined mixed butanols. An oscillator assembly is coupled to the internal baffle single pass reactor and has a reciprocating oscillator head selectively movable in a back and forth linear motion, and in communication with the process fluid such that the process fluid undergoes a general sinusoidal movement along the internal baffle single pass reactor.

20 Claims, 6 Drawing Sheets

Related U.S. Application Data (60) Provisional application No. 61/697,076, filed on Sep. 5, 2012.

(51) Int. Cl.
    *C07C 29/04* (2006.01)
    *C07C 31/12* (2006.01)

(52) U.S. Cl.
    CPC .......... *B01J 2219/0011* (2013.01); *B01J 2219/00094* (2013.01); *B01J 2219/00108* (2013.01); *B01J 2219/00777* (2013.01); *Y02P 20/582* (2015.11)

(58) Field of Classification Search
    CPC ...... B01J 19/006; B01J 19/185; Y02P 20/582; C07C 29/04
    See application file for complete search history.

(56) References Cited

U.S. PATENT DOCUMENTS

| | | | |
|---|---|---|---|
| 3,953,533 A | 4/1976 | Sommer et al. | |
| 3,989,762 A | 11/1976 | Ester | |
| 4,214,107 A | 7/1980 | Chang et al. | |
| 4,476,333 A | 10/1984 | Neier et al. | |
| 4,499,313 A | 2/1985 | Okumura et al. | |
| 4,507,512 A | 3/1985 | Okumura et al. | |
| 4,956,506 A | 9/1990 | Latimer | |
| 5,105,023 A | 4/1992 | Marler et al. | |
| 5,231,233 A | 7/1993 | Le et al. | |
| 5,302,762 A | 4/1994 | Yamashita et al. | |
| 6,429,268 B1 | 8/2002 | Xiongwei | |
| 6,861,494 B2 | 3/2005 | Debruin | |
| 2008/0277009 A1* | 11/2008 | Sprague | B01F 5/0451 138/38 |
| 2009/0245015 A1* | 10/2009 | Ni | B01F 11/0071 366/116 |
| 2009/0304890 A1 | 12/2009 | Ni et al. | |
| 2010/0010269 A1 | 1/2010 | Kolaczkowski | |
| 2010/0124145 A1 | 5/2010 | Ni et al. | |
| 2010/0216631 A1 | 8/2010 | Ni et al. | |
| 2011/0288060 A1 | 11/2011 | Ruecroft et al. | |
| 2014/0066667 A1 | 3/2014 | Arjah et al. | |

FOREIGN PATENT DOCUMENTS

| | | | |
|---|---|---|---|
| JP | 2007-230937 | * | 9/2007 |
| KR | 20080106516 A | | 12/2008 |
| WO | 2008122812 A2 | | 10/2008 |
| WO | 2013085964 A2 | | 6/2013 |
| WO | 2013170110 A1 | | 11/2013 |

OTHER PUBLICATIONS

ISRWO dated Jan. 2, 2017; International Application No. PCT/US2016/056015; International File Dated Oct. 7, 2016.
Caldeira et al., "Evaluation and Establishment of a Cleaning Protocol for the Production of Vanisal Sodium and Aspirin Using a Continuous Oscillatory Baffled Reactor", Organic Process Research & Development, 2009, pp. 1080-1087, vol. 13, No. 6, American.
Fabiyi et al., "The application of oscillatory flow mixing to photocatalytic wet oxidation", Journal of Photochemistry and Photobiology, 1999, pp. 17-24, vol. 129, Elsevier.
Gao et al., "Photooxidation of a model pollutant in an oscillatory flow reactor with baffles", Chemical Engineering Science, 2003, pp. 1013-1020, vol. 58, Elsevier Science Ltd.
Ghazi et al., "The Application of Pulsed Baffled Tube Photochemical Reactor (PBTPR) by Oscillatory Flow Mixing in Heterogeneous Photocatalysis", Prepared for presentation at the AIChE 2002 Annual Meeting Indiana Convention Center, Nov. 3-8, 2002, Pag.
http://en.wikipedia.org/wiki/User:Nitech2008/Oscillatory_baffled_reactor.
Mignard et al., "Modeling of droplet breakage probabilities in an oscillatory baffled reactor", Chemical Engineering Science, 2004, pp. 2189-2200, vol. 59, Elsevier.
Ni et al., "An Investigation of droplet size and size distribution in methylmethacrylate suspensions in a batch oscillatory-baffled reactor", Chemical Engineering Science, 1998, pp. 2903-2919, vol. 53, No. 16, Elsevier, Great Britain.
Ni et al., "Correlation of polymer particle size with droplet size in suspension polymerisation of methylmethacrylate in a batch oscillatory-baffled reactor", Chemical Engineering Science, 1999, pp. 841-850, vol. 54, Elsevier.
Ni et al., Flow Patterns and Oil-Water Dispersion in a 0.38 m Diameter Oscillatory Baffled Column, The Canadian Journal of Chemical Engineering, pp. 211-220, vol. 78.
Ni et al., "Inverse Phase Suspension Polymerization of Acrylamide in a Batch Oscillatory Baffled Reactor", Journal of Applied Polymer Science, 2000, pp. 1669-1676, vol. 76, John Wiley & Sons, Inc.
Ni et al., "On the evaluation of droplet breakage and coalescence rates in an oscillatory baffled reactor" Chemical Engineering Science, 2002, pp. 2101-2114, vol. 57, Elsevier.
Ni et al., "Polymer product engineering utilizing oscillatory baffled reactors", Powder Technology, 2002, pp. 281-286, vol. 124, Elsevier.
Ni et al., "Suspension Polymerization of Acrylamide in an Oscillatory Baffled Reactor: from Drops to Particles", AIChE Journal, Aug. 2001, pp. 1746-1757, vol. 47, No. 8.
Ni, "Continuous Oscillatory Baffled Reactor Technology", Innovations in Pharmaceutical Technolygy, 2006, pp. 90-96.
Phan et al., "Development and evaluation of novel designs of continuous mesoscale oscillatory baffled reactors", Chemical Engineering Journal, 2010, pp. 212-219, vol. 159, Elsevier.
Sherrington et al., "Gram-Scale Synthesis of Suspension-Polymerized Styrene-Divinylbenzene-Based Resins Using an Oscillatory Baffled Reactor", Angewandte Chemie, 2002, pp. 3808-3811, vol. 114, No. 19, Wiley-VCH.
Wiese et al., "A new reactor design for catalytic fluid-fluid multiphase reactions", Catalysis Today, 2003, vol. 79, pp. 97-103, Elsevier.
Wilson et al., "A Study of a Phase Transfer Catalytic Reaction between N-Butyl Bromide and Sodium Phenolate in an Oscillatory Baffled Reactor" Studies in Surface Science and Catalysis, 2001, pp. 481-487, vol. 133, Elsevier.
Wilson et al., "Butylation of Phenylacetonitrile in an Oscillatory Baffled Reactor", Ind. Eng. Chem. Res., 2005, pp. 8663-8670, vol. 44, No. 23, American Chemical Society Published on Web.
Wilson et al., "On the Investigation of a Phase-Transfer Catalysis Reaction in an Oscillatory Baffled Reactor", Ind. Eng. Chem. Res., 2001, pp. 5300-5304, vol. 40, American Chemical Society, Published on Web.
Zhang et al., "A Study of Oil-Water Dispersion in a Pulsed Baffled Reactor", J. Chem. Tech. Biotechnol, 1996, pp. 305-311, vol. 66, SCI, Great Britain.
Zhang et al., "Study on Oscillatory Flow Reactor and Its Application in Flocculating Oricess for Sewage Treatment", Petroleum Refinery Engineering, 2005, pp. 56-58, vol. 35, No. 4.
PCT International Search Report and the Written Opinion of the International Searching Authority dated Dec. 20, 2013; International Application No. PCT/US2012/044189; International File Dated Jun. 5, 2013.

* cited by examiner

OLEFIN HYDRATION PROCESS USING OSCILLATORY BAFFLED REACTOR

CROSS-REFERENCE TO RELATED PATENT APPLICATIONS

This application is a continuation-in-part of and claims priority to and the benefit of U.S. patent application Ser. No. 14/016,798, now U.S. Pat. No. 9,187,388 titled "Olefin Hydration Process Using Oscillatory Baffled Reactor," filed Sep. 3, 2013, which claims priority to and the benefit of U.S. Provisional Application No. 61/697,076, filed Sep. 5, 2012. For purposes of United States patent practice, this application incorporates the full disclosure of each such application by reference in its entirety.

BACKGROUND OF THE INVENTION

1. Field of the Invention

The field of invention relates to the production of butanol. More specifically, the field relates to the production of butanol via butene hydration.

2. Description of the Related Art

Butanol is an effective alternative to traditional oxygenates and fuel-stock expanders, which includes methyl tent-butyl ether and ethanol. Butanol not only contributes octane-rating enhancement but also supplies incorporated oxygen into the fuel mix. Mixed or blended butanols are also relatively inexpensive.

The primary means for producing butanol, especially mixed butanols, is through a butene hydration process. Known butene hydration processes include liquid-liquid biphasic systems. Butenes and water are immiscible in one another at low relative concentrations (both butene-in-water and water-in-butene) systems. Elevated operating conditions do not alleviate the immiscibility. The immiscibility of the reactants is one reason for the known low single-pass conversion rate.

In addition, the immiscibility also affects the distribution of the hydration catalyst. Typical hydration catalysts prefer either the aqueous phase or the hydrocarbon phase—usually not both. This poor distribution of hydration catalyst does not foster catalytic reactions throughout the biphasic system but rather predominantly in only one phase.

A need therefore exists to improve the single-pass conversion yield of butene into butanol in butene hydration systems and processes.

SUMMARY OF THE INVENTION

A butanol production system for producing refined mixed butanols from water and mixed butenes includes an internal baffle single pass reactor having an internal fluid conduit defined by an internal wall and an operating length between a proximal end and a distal end, the internal fluid conduit selectively containing and mixing a process fluid comprising water, mixed butenes and mixed butanols, to form a crude product. The internal baffle single pass reactor also includes internal flow baffles located along at least a portion of the operating length of the internal fluid conduit, the internal flow baffles being ring shaped and secured the internal wall. Baffled cells are located consecutively along the operating length and defined at an outer diameter by the internal wall and at a first end and a second end by the internal flow baffles, wherein one of the internal flow baffles defines both the second end of one of the baffled cells and a first end of an adjacent baffled cell. A separation system is in fluid communication with the internal baffle single pass reactor, oriented for selectively receiving the crude product and separating water and mixed butenes from the crude product such that refined mixed butanols is produced. An oscillator assembly is coupled to the proximal end of the internal baffle single pass reactor, the oscillator assembly having a reciprocating oscillator head selectively movable in a back and forth linear motion, and in communication with the process fluid such that the process fluid undergoes a general sinusoidal movement along the internal baffle single pass reactor.

In alternate embodiments, each of the internal flow baffles can be formed of a disk shaped plate with an orifice extending through the plate. An outer diameter of the disk shaped plate can be fixed to the internal wall. The orifice can be sized and positioned through the plate to generate vortices within the process fluid in the baffled cells. The baffled cells can be located along the entire operating length of the internal fluid conduit.

In other alternate embodiments, an outer diameter of the oscillator head can slidingly engage the internal wall. The separation system can be in fluid communication with the distal end of the internal fluid conduit or can be in fluid communication with at least one of the baffled cells. The oscillator head can have a reciprocating frequency of 2 to 5 Hertz and can have a reciprocating amplitude of 20-40 millimeters. The oscillator assembly can include an external motion driver mechanically coupled to, and selectively driving, the oscillator head. The oscillator assembly can include an oscillator seal section sealingly engaging the internal baffle single pass reactor and a process fluid oscillator member, the process fluid oscillator member mechanically linking the external motion driver to the oscillator head.

In another embodiment of this disclosure, a method for producing refined mixed butanols from a combination of water and mixed butenes includes providing an internal baffle single pass reactor. The internal baffle single pass reactor has an internal fluid conduit defined by an internal wall and an operating length between a proximal end and a distal end. Internal flow baffles are located along at least a portion of the operating length of the internal fluid conduit, the internal flow baffles being ring shaped and secured the internal wall. Baffled cells are located consecutively along the operating length and are defined at an outer diameter by the internal wall and at first and second ends by the internal flow baffles, wherein one of the internal flow baffles defines both the second end of one of the baffled cells and a first end of an adjacent baffled cell. A process fluid comprising, mixed butenes, water and mixed butanols is passed through the internal baffle single pass reactor. The process fluid are mixed within the internal baffle single pass reactor to form a crude product by inducing a generally sinusoidal movement in the process fluid along the internal baffle single pass reactor with an oscillator assembly that is coupled to the proximal end of the internal baffle single pass reactor, the oscillator assembly having a reciprocating oscillator head selectively movable in a back and forth linear motion. The water and the mixed butenes are separated from the crude product in a separation system that is in fluid communication with the internal baffle single pass reactor to produce refined mixed butanols.

In alternate embodiments, the step of mixing the process fluid within the internal baffle single pass reactor can include inducing vortices in the process fluid in the baffled cells by pushing the process fluid past the internal flow baffles. The process fluid can be transferred to the separation system at the distal end of the internal fluid conduit or can be transferred to the separation system from within at least one of the baffled cells to the separation system.

In other alternate embodiments, the oscillator assembly can be operated with a reciprocating frequency of 2 to 5 Hertz and a reciprocating amplitude of 20-40 millimeters. The oscillator head can be driven with an external motion driver that is mechanically coupled to the oscillator head. The internal baffle single pass reactor and a process fluid oscillator member can be sealingly engaged with an oscillator seal section that mechanically links the external motion driver to the oscillator head.

BRIEF DESCRIPTION OF THE DRAWINGS

These and other features, aspects, and advantages of the present invention are better understood with regard to the following Detailed Description of the Preferred Embodiments, appended Claims, and accompanying Figures, where:

In the accompanying Figures, similar components or features, or both, may have the same reference label. The Figure and its description facilitate a better understanding of the butanol production system and its method of use. In no way should the Figure limit or define the scope of the invention. The Figure is a simple diagram for ease of description. Those of ordinary skill in the art understand that such systems are complex structures with ancillary equipment and subsystems that render them operable for their intended purpose.

DETAILED DESCRIPTION OF THE PREFERRED EMBODIMENTS

The Specification, which includes the Summary of Invention, Brief Description of the Drawings and the Detailed Description of the Preferred Embodiments, and the appended Claims refer to particular features (including process or method steps) of the invention. Those of skill in the art understand that the invention includes all possible combinations and uses of particular features described in the Specification. Those of skill in the art understand that the invention is not limited to or by the description of embodiments given in the Specification. The inventive subject matter is not restricted except only in the spirit of the Specification and appended Claims.

Those of skill in the art also understand that the terminology used for describing particular embodiments does not limit the scope or breadth of the invention. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur. "Operable" and its various forms means fit for its proper functioning and able to be used for its intended use. "Associated" and its various forms means something connected with something else because they occur together or that one produces the other.

Spatial terms describe the relative position of an object or a group of objects relative to another object or group of objects. The spatial relationships apply along vertical and horizontal axes. Orientation and relational words including "upstream" and "downstream" and other like terms are for descriptive convenience and are not limiting unless otherwise indicated.

Where the Specification or the appended Claims provide a range of values, it is understood that the interval encompasses each intervening value between the upper limit and the lower limit as well as the upper limit and the lower limit. The invention encompasses and bounds smaller ranges of the interval subject to any specific exclusion provided. "Substantially free" means less than 1% by the indicated unit of measure. "Significant" means equal to or greater than 10% by the indicated unit of measure.

Where reference is made in the Specification and appended Claims to a method comprising two or more defined steps, the defined steps can be carried out in any order or simultaneously except where the context excludes that possibility.

FIGS. 1A-1B

Figure 1A:
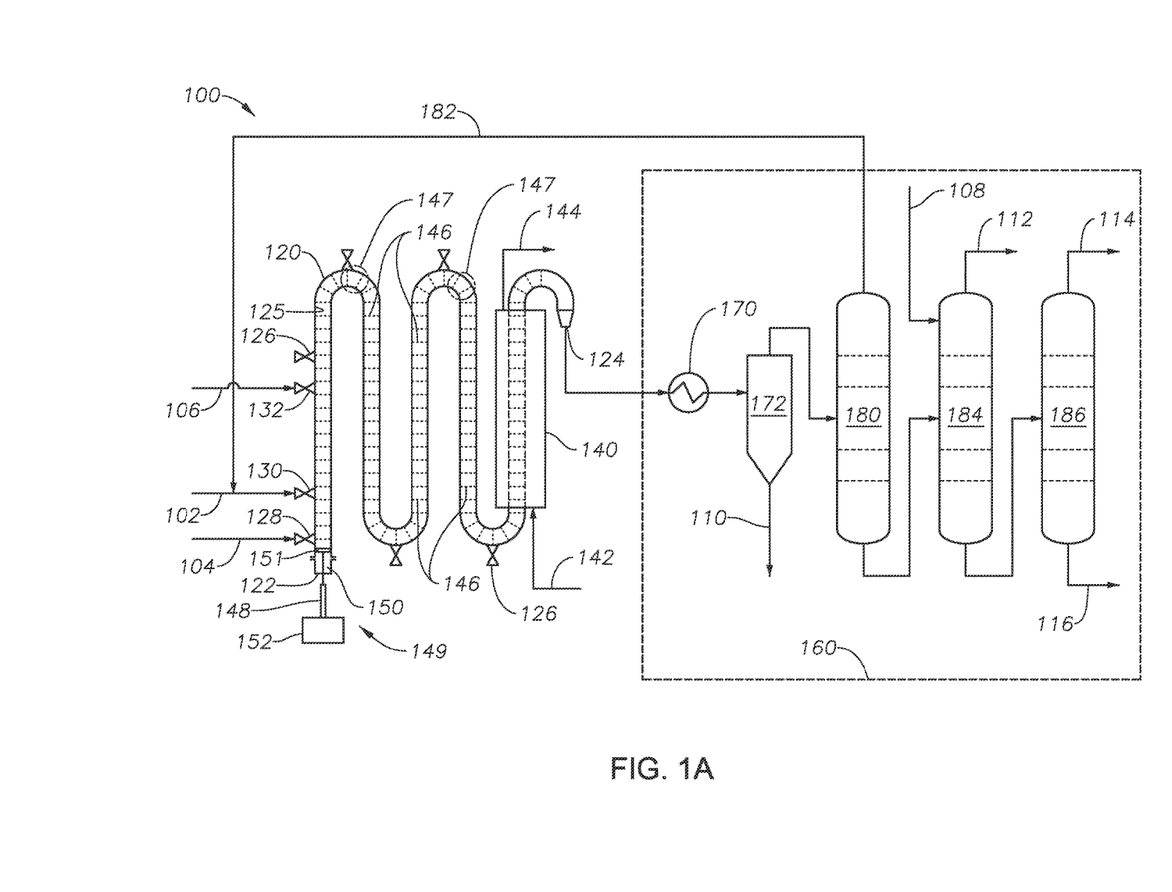
FIGS. 1A-1B are process flow diagrams of embodiments of the butanol production system.
Figure 1B:
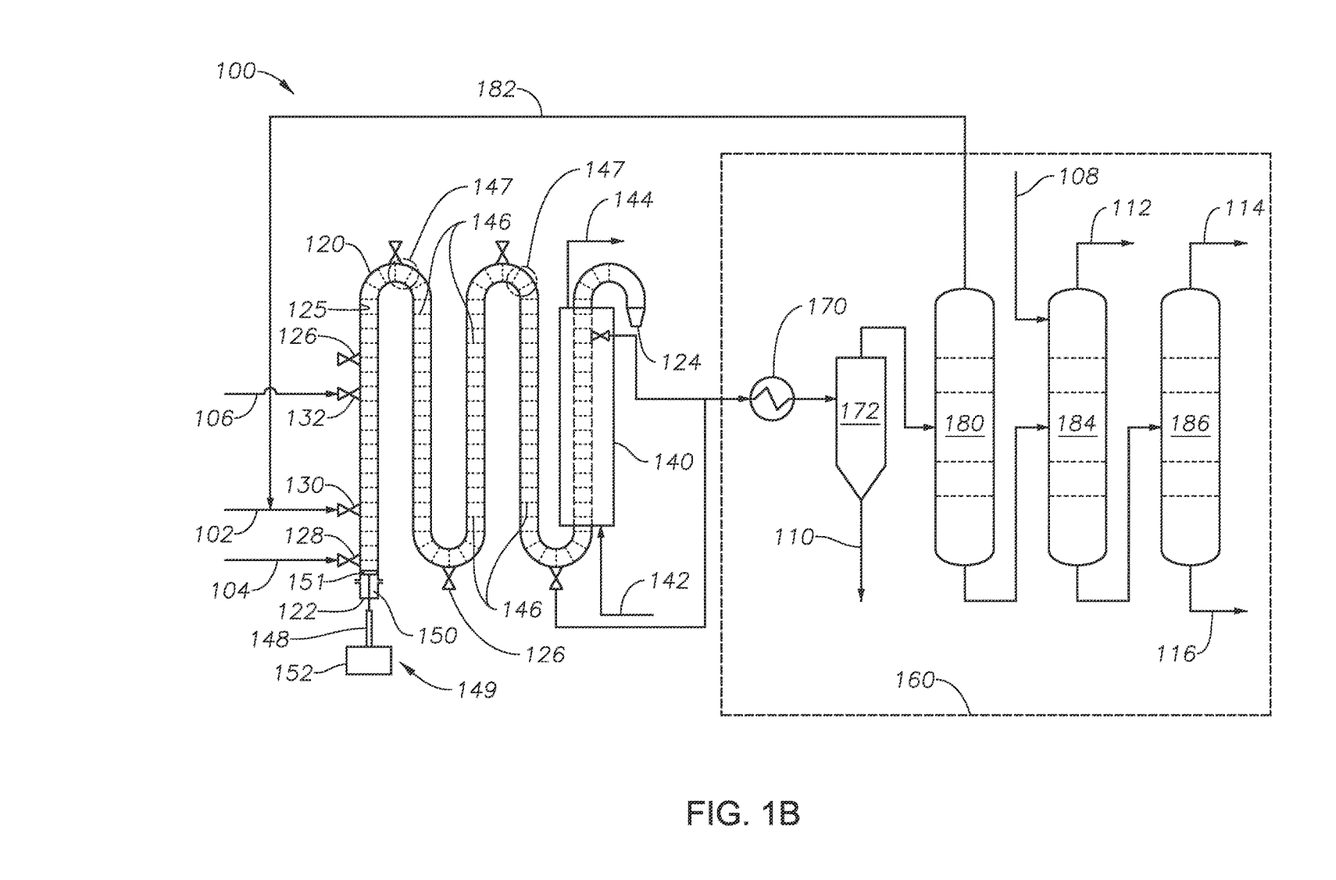

FIGS. 1A-1B include a process flow diagram of an embodiment of the butanol production system. The butanol production process of FIGS. 1A-1B introduce several feeds into butanol production system 100 through feed lines, including mixed butene feed 102, water feed 104, hydration catalyst feed 106 and entrainer feed 108. Butanol production system 100 produces several products through product lines, including waste catalyst 110, production water 112, butanol product 114 and spent entrainer 116.

Butanol production system 100 includes several units that support the conversion of butenes to butanols and the production of a refined butanols product. Internal baffle single pass reactor 120 supports catalytically induced hydration of butenes into mixed butanols. Mixed butene feed 102, water feed 104 and hydration catalyst feed 106 all enter butanol production system 100 through internal baffle single pass reactor 120. Internal baffle single pass reactor 120 produces a crude product stream useful for recovering produced mixed butanol.

Internal baffle single pass reactor 120 contains a process fluid that is a mixture of reactants, catalyst and reaction products. The process fluid traverses internal baffle single pass reactor 120 from proximal end 122 to distal end 124 via an internal fluid conduit defined by internal wall 125. The composition of the process fluid changes along the operating length of internal baffle single pass reactor 120 as the butene hydration reaction occurs, forming product mixed butanols and consuming reactants water and mixed butenes.

Separation system 160 is in fluid communication with internal baffle single pass reactor 120. Separation system 160 is oriented for selectively receiving the crude product and separating water and mixed butenes from the crude product such that refined mixed butanols is produced. In separation system 160 (dashed box), cooler 170 couples to internal baffle single pass reactor 120 and is operable to receive the crude product from internal baffle single pass reactor 120 and reduce the crude product temperature for separations processing. In the embodiment of FIG. 1A, separation system 160 couples to, and is in fluid communication with, distal end 124 of internal baffle single pass reactor 120. In the embodiment of FIG. 1B, separation system 160 couples to, and is in fluid communication with other areas of internal baffle single pass reactor 120. As an example, separation system 160 can couple to internal baffle single pass reactor 120 at least one of the baffled cells 147.

In butanol production system 100, cyclone 172 couples to cooler 170, receives the cooled crude product, and removes any remaining heterogeneous hydration catalyst. Cyclone 172 produces both a spent catalyst through waste catalyst 110 and a catalyst-free crude product.

Debutenizer column 180 couples to cyclone 172, receives the catalyst-free crude product, and removes unreacted butenes. Debutenizer column 180 produces recovered butenes and a butene-free crude product. The recovered butenes are recycled to the proximal end of internal baffle single pass reactor 120 via butene recycle 182 by butanol production system 100.

Butanols extraction column 184 couples to debutenizer column 180, receives the butene-free crude product, and also receives entrainer through entrainer feed 108. Butanols extraction column 184 operates by using the introduced entrainer to extract butanols from the water phase of the butene-free crude product, forming a water phase that is butanol poor and an entrainer and butanol phase that is rich in butanol. Water passes from butanols extraction column 184 via production water 112. The entrainer and butanol phase passes as the bottoms of butanols extraction column 184.

Butanols separation column 186 couples to butanols extraction column 184, receives the entrainer and butanol phase, and separates butanols from the entrainer. Butanols separation column 186 produces the refined mixed butanols that is substantially free of water, butenes and the entrainer. The refined butanols mixture passes from butanols separation column 186 via butanol product 114. Recovered entrainer passes from butanols separation column 186 via spent entrainer 116.

As shown in FIGS. 1A-1B, the configuration of internal baffle single pass reactor 120 is a serpentine-shaped conduit with proximal end 122 and distal end 124, with distal end 124 coupling to cooler 170. Several ports 126 are for accessing the interior of the internal baffle single pass reactor 120. Several injection ports provide feed access to the interior of the internal baffle single pass reactor 120, including water injection port 128, butene injection port 130 and catalyst injection port 132.

The process fluid also provides latent heat for supporting the hydration reaction by conveying heat transferred into the reactor through external heat exchange systems. For example, FIGS. 1A-1B show temperature control jacket 140 enveloping a portion of internal baffle single pass reactor 120. Temperature control jacket 140 is operable to provide heat to the enveloped portion of internal baffle single pass reactor 120 to encourage the hydration reaction in the process fluid. Temperature control fluid supply conduit 142 introduces fresh temperature control fluid and temperature control fluid return conduit 144 passes exhausted temperature control fluid.

Internal baffle single pass reactor 120 has internal flow baffles 146 along its operable length. Each internal flow baffle 146 can be a ring shaped member that is secured to internal wall 125 so that each internal flow baffle is fixed an un-movable within internal baffle single pass reactor 120. Baffled cells 147 are located between successive internal flow baffles 146. Baffled cells 147 are defined at an outer diameter by internal wall 125 and at a first end and a second end by internal flow baffles 146, wherein one of the internal flow baffles 146 defines both the second end of one of the baffled cells 147 and a first end of an adjacent baffled cell 147. Baffled cells 147 located consecutively along the operating length of internal baffle single pass reactor 120.

Internal flow baffles 146 disrupt the fluid momentum and alter the flow path of the process fluid as it flows through internal baffle single pass reactor 120. The disruption of the flow momentum and modification of the fluid flow path causes intimate mixing of the butenes, water and catalyst together in the process fluid to occur in baffled cell 147. Fluid flow not in alignment with the central axis of internal baffle single pass reactor 120 also facilitates heat transfer into the fluid by conveying heat from the internal wall 125 of internal baffle single pass reactor 120 into the bulk process fluid. Internal flow baffles 146 also increase process residence time, which improves conversion of butenes into butanol.

Oscillator assembly 149 is coupled to proximal end 122 of internal baffle single pass reactor 120. Oscillator assembly 149 includes process fluid oscillator member 148 that is located near proximal end 122 of internal baffle single pass reactor 120. Oscillator assembly 149 also includes oscillator seal section 150 that sealingly engaging the internal baffle single pass reactor 120 and a process fluid oscillator member 148 that mechanically links external motion driver 152 to the oscillator head 151. Process fluid oscillator member 148 couples to internal baffle single pass reactor 120 via oscillator seal section 150 such that process fluid oscillator member 148 passes from the exterior to the interior of internal baffle single pass reactor 120 without exposing external contaminants to the process fluid and without leaking the process fluid to the external environment. Process fluid oscillator member 148 couples with the internal wall 125 of internal baffle single pass reactor 120 at oscillator head 151 so that an outer diameter of oscillator head 151 slidingly engages internal wall. Oscillator head 151 reciprocates in a back and forth linear motion, and is in communication with the process fluid such that the process fluid undergoes a general sinusoidal movement along the length of the internal baffle single pass reactor 120. Oscillator head 151 can be in direct contact with the process fluid or can be in indirect communication with the process fluid, such as by way of a diaphragm or other member that can transfer motion of oscillator head 151 to generally sinusoidal movement of the process fluid.

Change to the relative position of process fluid oscillator member 148 imparts a position change in the process fluid due to its contact with oscillator head 151 and the incompressibility of the process fluid. The position change in the process fluid imparts unsteadiness in the flow momentum of the process fluid flow along the operable length of internal baffle single pass reactor 120. The unsteadiness in the process fluid flow enhances mixing and heat absorption. The pushing and pulling of the incompressible process fluid causes the flow of the process fluid to surge and retreat relative to a fixed position within the interior of internal baffle single pass reactor 120. This mixing of the process fluid within internal baffle single pass reactor 120 forms a crude product by inducing a generally sinusoidal movement in the process fluid along internal baffle single pass reactor 120 with oscillator assembly 149.

Oscillator assembly 149 also includes external motion driver 152. External motion driver 152 is coupled to oscillator head 151 by way of process fluid oscillator member 148 and can be used to selectively drive process fluid oscillator member 148 and oscillator head 151. The configuration of oscillator seal section 150, the coupling to external motion driver 152 and the contact that oscillator head 151 has with the internal wall 125 of internal baffle single pass reactor 120 restricts process fluid oscillator member 148 to a limited range of motion. Process fluid oscillator member 148, when operable, moves oscillator head 151 in a back-and-forth type of linear direction.

FIG. 2

Figure 2:
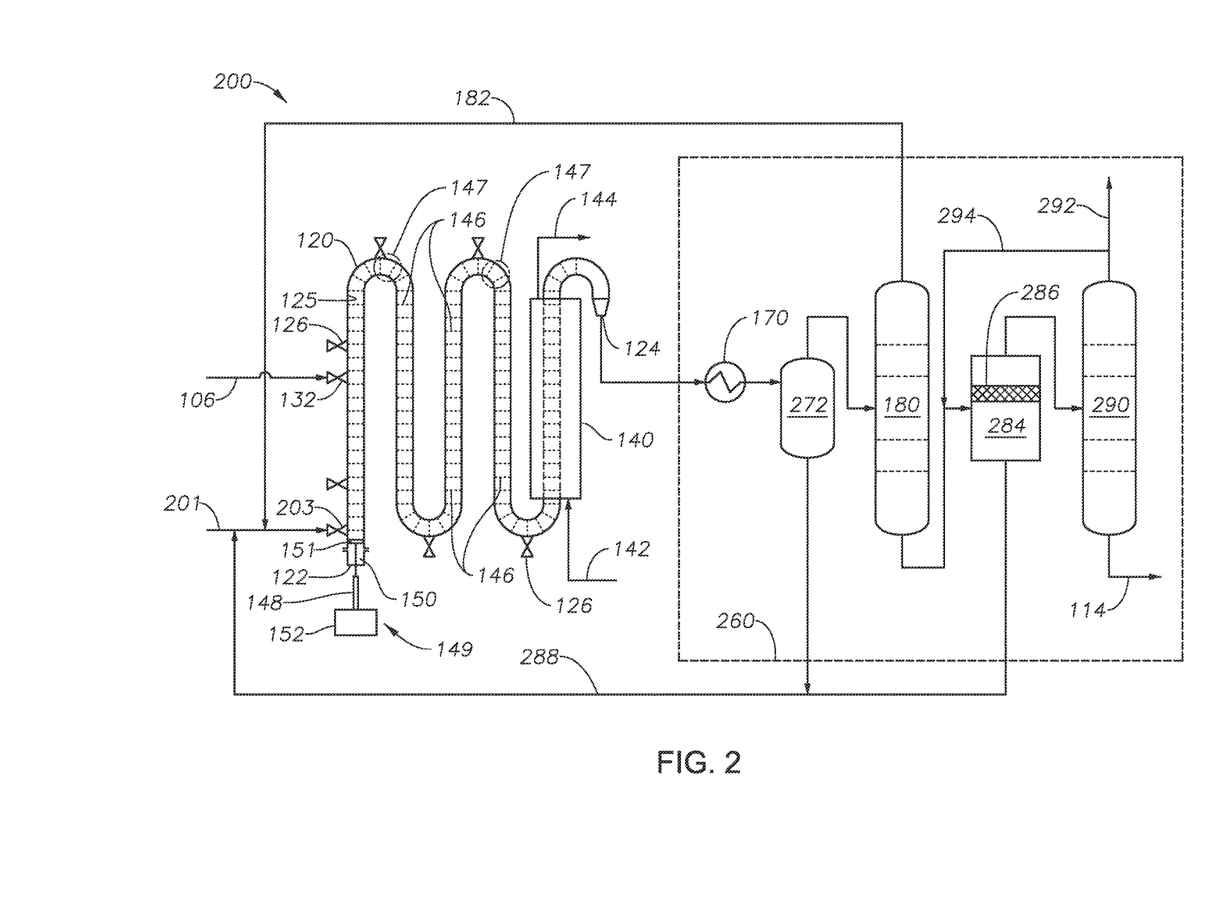
FIG. 2 is a process flow diagram of another embodiment of the butanol production system.

FIG. 2 is a process flow diagram of another embodiment of the butanol production system. The butanol production process of FIG. 2 introduces several feeds into butanol production system 200, including combined mixed butenes and water feed 201 and hydration catalyst feed 106. Combined mixed butenes and water feed 201 enters internal baffle single pass reactor 120 through butene and water injection port 203. Butanol production system 200 produces several products, including refining vent 292 and butanol product 114. System recycle streams butene recycle 182 and water recycle 288 both contribute to minimizing the amount of makeup mixed butenes and water in water feed 201.

Separation system 260 in FIG. 2 is configured differently than separation system 160 in FIGS. 1A-1B. High pressure (HP) water separator 272 couples to cooler 170, receives the cooled crude product, and removes a significant portion of the water, forming a water-lean crude product. The recovered water and hydration catalyst pass through water recycle 288 for reintroduction into internal baffle single pass reactor 120.

Debutenizer column 180 couples to HP water separator 272, receives the water-lean crude product, and operates to remove unreacted butenes from the water-lean crude product, forming a butene-free crude product. The recovered butenes pass to the proximal end of internal baffle single pass reactor 120 via butene recycle 182.

Pervaporation unit 284 includes pervaporation membrane 286. Pervaporation unit 284 couples to debutenizer column 180, receives the butene-free crude product and is operable to separate butanols as a permeate using pervaporation membrane 286 from the butene-free crude product. Pervaporation unit 284 forms a butanol vapor on the permeate side and a retentate made of mostly water on the feed side of pervaporation membrane 286. The water retentate passes to internal baffle single pass reactor 120 through water recycle 288.

Butanols separation column 290 couples to pervaporation unit 284, receives the butanol vapor and operates to refine the butanol vapor into a refined mixed butanols. The refined mixed butanols is substantially free of water and butenes and is conveyed via butanol product 114. Butanols separation column 290 vents lights and incondensable gases. A portion of the lights and incondensable gases are vented through the stream of refining vent 292 and the remainder is recycled to pervaporation unit 284 through distillation recycle 294 for butanol recovery.

FIG. 3

Figure 3:
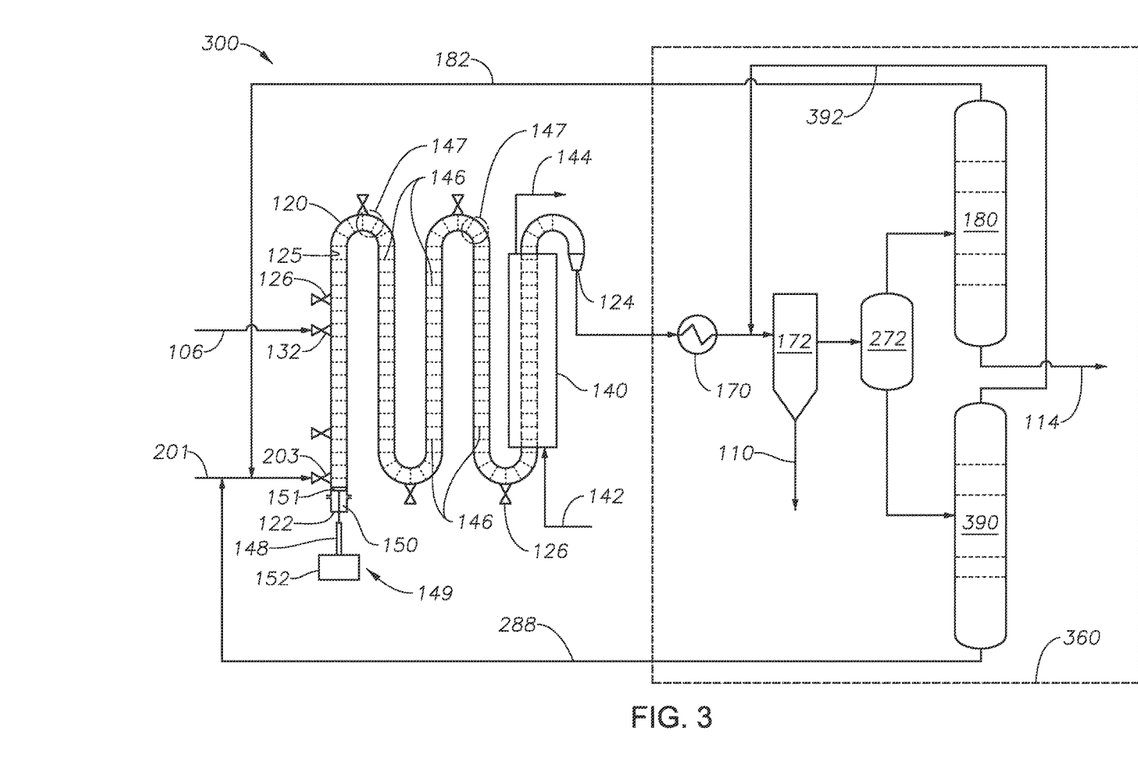
FIG. 3 is a process flow diagram of another embodiment of the butanol production system.

FIG. 3 is a process flow diagram of another embodiment of the butanol production system. The butanol production process of FIG. 3 introduces feeds similar to those shown for the process of FIG. 2. Butanol production system 300 produces several products, including waste catalyst 110 and butanol product 114. System 300 recycle streams butene recycle 182 and water recycle 288 both contribute to minimizing the amount of makeup mixed butenes and water in combined feed 201.

Separation system 360 in FIG. 3 is configured differently than separation systems 160 and 260. Cyclone 172 couples to cooler 170, receives the cooled crude product, and removes any remaining heterogeneous hydration catalyst, polymer and other solids via waste catalyst 110. Cyclone 172 produces both a spent catalyst through waste catalyst 110 and a catalyst-free crude product. High pressure (HP) water separator 272 couples to cyclone 172, receives the catalyst-free crude product, and under high pressure separates the organic phase, which contains the butanols and butenes, from the aqueous phase. The aqueous phase still contains some butanols but far less than the organic phase. Debutenizer column 180 couples to HP water separator 272, receives the organic butanol and butenes phase, and separates the organic phase into recyclable butenes and the refined mixed butanols. The recovered butenes are conveyed to the front of the process via butene recycle 182 and the refined mixed butanols are passed via butanol product 114. Azeotropic column 390 couples to HP water separator 272, receives the water phase and separates the water phase into a butanol/water azeotrope and recyclable water. The butanol/water azeotrope is recycled to the front of separation system 360 via butanol/water recycle 392 and the recyclable water is conveyed to the front of the process via water recycle 288.

FIG. 4

Figure 4:
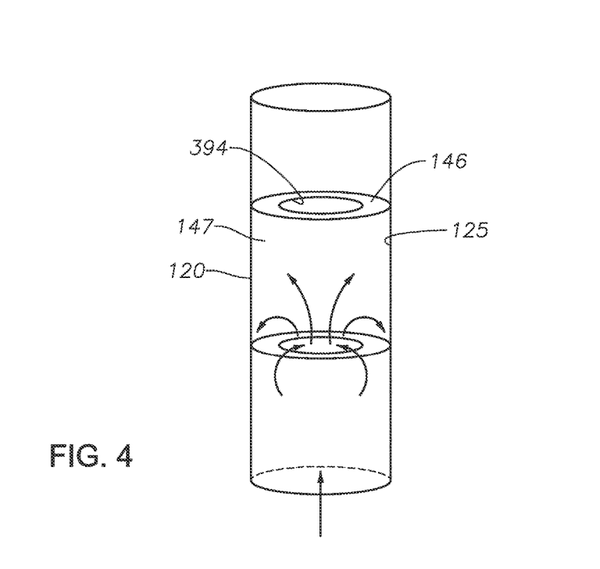
FIG. 4 is a schematic detail view of a portion of the internal baffle single pass reactor in accordance with an embodiment of this disclosure.

FIG. 4 is a detail view of an embodiment of the internal flow baffles 146 along the operable length of internal baffle single pass reactor 120. In the example embodiment of FIG. 4, each of the internal flow baffles 146 can be formed of a disk shaped plate with an orifice 394 extending through the plate. An outer diameter of the disk shaped plate is fixed to internal wall 125. As process fluid passes through baffled cells 147, the interaction of process fluid with internal flow baffles 146 generates vortices within the process fluids. Orifice 394 can be sized and positioned through each internal flow baffle 146 to generate vortices within the process fluid in baffled cells 147 that results in optimized mixing of the process fluid. As an example, the diamater of orifice 394 relative to the diameter of internal flow baffle 146 as well as the location of orifice 394 through internal flow baffle 146 can be selected optimize the mixing of the process fluid.

As process fluid flows through internal baffle single pass reactor 120, some of the process fluid passes through orifice 394 of an internal flow baffle 146. Other of the process fluid contacts the solid ring portion of internal flow baffle 146 and is redirected within a baffled cell 147 to form vortices within the process fluid. The vortices formed in baffled cells 147 improve mixing of the process fluid.

FIG. 5

Figure 5:
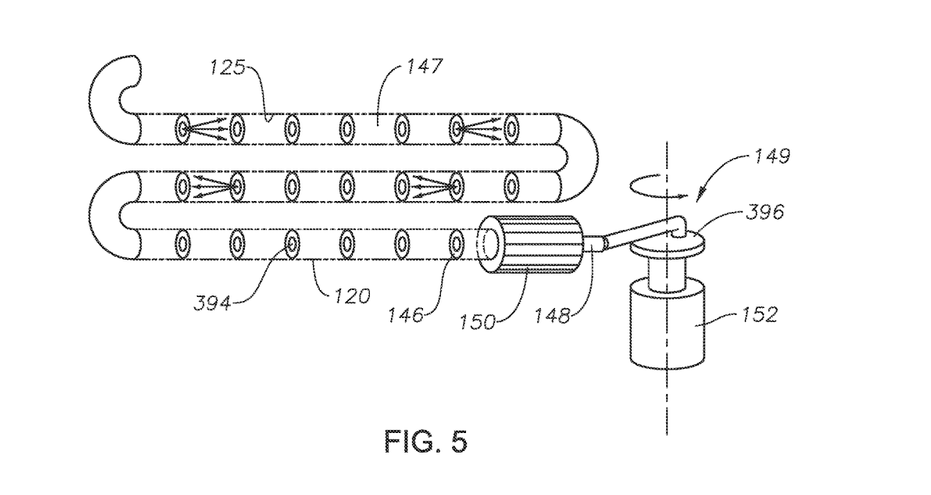
FIG. 5 is a schematic view of the internal baffle single pass reactor and external motion driver in accordance with an embodiment of this disclosure.

FIG. 5 shows an example embodiment of external motion driver 152 in accordance with an embodiment of this disclosure. In the example of FIG. 5, external motion driver 152 includes a rotary disk 396. A first end of process fluid oscillator member 148 is connected to rotary disk 396. In the embodiment of FIG. 5, process fluid oscillator member 148 is a jointed member. As external motion driver 152 rotates, a second end of process fluid oscillator member 148 moves linearly back and forth relative to proximal end 122 of internal baffle single pass reactor 120. The second end of process fluid oscillator member 148 is attached to oscillator head 151 and causes oscillator head 151 to reciprocate within internal baffle single pass reactor 120.

As oscillator head 151 moves farther into internal baffle single pass reactor 120, oscillator head 151 pushes process fluid in a direction from proximal end 122 towards distal end 124. As oscillator head 151 moves in an opposite direction, towards proximal end 122, oscillator head 151 pushes process fluid in a direction from distal end 124 proximal end 122, as shown with the directional arrows of FIG. 5. Due to this back and forth motion of oscillator head 151, the process fluid moves in a general overall sinusoidal back and forth motion within internal baffle single pass reactor 120. In this way, an oscillatory movement is superimposed upon all the reactants in internal baffle single pass reactor 120. This sinusoidal type movement enables unique radial mixing.

Process Fluid and Crude Product

The process fluid is a dual-phase process of immiscible butenes and water at the operating conditions of the butanol production process while inside the internal baffle single pass reactor. At any given point along the operating length of the reactor, the process fluid includes butenes, water, optionally butene hydration catalyst and butene hydration products, especially butanols.

The butene hydration reaction occurs in the internal baffle single pass reactor. The process fluid supports the hydration reaction of mixed butenes into mixed butanols in the presence of the butene hydration catalyst in the reactor. As part of the butanol production process, the process fluid passes from the reactor at a location proximate to the distal end of the reactor as crude product.

The crude product is a combination of product butanols, water, butenes and optionally butene hydration catalyst, which may be still active. The crude product is the process fluid after passing from the distal end of the internal baffle single pass reactor.

Mixed Butenes

Mixed butenes are introduced as a reactant as part of the butanol production process. The mixed butenes can be purified or can come from a source within a petrochemical refinery, including as a product of a FCC unit or a thermal cracking unit, a raffinate from a MTBE or TBA process, a fraction of a liquefied petroleum gas (LPG), or as a combined stream from several of like sources. Mixed butenes include one or more of 1-butene, one or both 2 butenes (that is, cis or trans), and isobutylene. Mixed butenes can also include other alkanes and alkenes.

In an embodiment of the butanol production produces, the mixed butenes comprise 1-butene. An embodiment of the butanol production process includes where the mixed butenes consists essentially of 1-butene. Fresh or "make-up" 1-butene is preferably polymerization-grade. Fresh 1-butene is at least 99 vol. % 1-butene, or 99.5 vol. % 1-butene, or 99.9 vol. % 1-butene, or 99.95 vol. % 1-butene, or even higher purity. Impurities in the fresh 1-butene are at or less than 5 ppm by volume.

Recycling butenes from other parts of the butanol production system maximizes butene conversion efficiency. Butanol production system includes a separations system that selectively separates recoverable mixed butenes from the crude product. An embodiment of the butanol production system includes where the butanol production system is operable to introduce the selectively separated mixed butenes into the interior baffle single pass reactor. An embodiment of the butanol production process includes operating the butanol production system such that the separately selectively separated mixed butenes is introduced into the internal baffle single pass reactor. Recycled butenes can have a lower compositional purity than fresh butenes since the recycled material is already internal to the butanol production system and cannot introduce new inert or contaminant materials.

Introduction of mixed butenes occurs as a pressurized gas, a liquid, a supercritical fluid or combinations thereof. The critical temperature of 1-butene is 146.4° C. and the critical pressure is 40.2 bar. The critical temperature of isobutylene is 144.7° C. and the critical pressure is 40.01 bar. Pre-heating the introduced mixed butene provides heat to the process fluid that encourages hydration.

Water

Water is introduced as a reactant as part of the butanol production process. Fresh or makeup water introduced into the butanol production system is at least 99 vol. % water, or 99.5 vol. % water, or 99.9 vol. % water, or 99.95 vol. % water, or even higher purity. The water should be degassed, demineralized and deionized to not introduce contaminants into the butanol production system. Impurities are at or less than 5 ppm by volume.

Recycling water from other parts of the butanol production system minimizes the amount of introduced makeup water. Water is typically used in excess in the butanol production process. The separation system selectively separates recoverable water from the crude product passing from the internal baffle single pass reactor. An embodiment of the butanol production system includes where the butanol production system is operable to introduce the selectively separated water into the interior baffle single pass reactor. An embodiment of the butanol production process includes operating the butanol production system such that the separately selectively separated water is introduced into the internal baffle single pass reactor. When using a homogeneous catalyst that has not been neutralized, the recycled water can convey the active hydration catalyst to the front of the butanol production system. An embodiment of the butanol production process includes where the separately selectively separated water also comprises a homogeneous butene hydration catalyst.

An embodiment of the butanol production process includes where the water and the mixed butenes are introduced into the internal baffle single pass reactor such that the molar ratio value of water to 1-butene is in a range of from about 1 to about 21.

Hydration Catalysts

A butene hydration catalyst is introduced as a reactant as part of the butanol production process when the butanol production system does not include a fixed heterogeneous acid catalyst. The introduction of a butene hydration catalyst is optional when the butanol production system does not include a fixed heterogeneous acid catalyst. An embodiment of the butanol production process includes introducing the butene hydration catalyst into the internal baffle single pass reactor of the butanol production system such that the process fluid forms proximate to the proximal end, where the butene hydration catalyst is selected from a homogeneous acid, a heterogeneous acid, and combinations thereof.

Useful butene hydration catalysts that are homogeneous acids include, for example, sulfuric acids and phosphoric acids. An embodiment of the butanol production process includes where the butene hydration catalyst introduced is homogeneous. Examples of useful phosphoric acids include orthophosphoric acid, polyphosphoric (PPA) and superphosphoric acids (SPA). Polyphosphoric acids are oxyacids of phosphorous having the general chemical formula $H(PO_3H)_nOH$, where n is an integer representing the number of phosphoric units in the molecule. Commercial mixtures of PPAs have blends of ortho- (n=1), pyro- (n=2), tri- (n=3), tetra- (n=4) and higher-order condensed chain acids. PPA concentrations in the range of from about 95% to about 118% phosphoric acid ($H_3PO_4$) concentration equivalents represents the equivalent amount of phosphoric acid that forms upon complete hydrolysis of the polyphosphoric acid. An example is orthophosphoric acid ($H_3PO_4$) (Sigma-Aldrich Corp.; St. Louis, Mo.).

Useful butene hydration catalysts also include heterogeneous acidic catalysts. An embodiment of the butanol production process includes where the butene hydration catalyst introduced is heterogeneous. Such acids have acid-functionalities incorporated into their metallic, ceramic, particulate or polymeric structure. Recovery processes, including evaporation, vaporization, distillation and centrifuge systems can extract the solid catalyst from the process fluid or crude product. An embodiment of the butanol production process includes operating the butanol production system such that the separation system separately selectively separates the butene hydration catalyst from the crude product, where the butene hydration catalyst is a heterogeneous catalyst. Examples include D008-1 and D008-2 (KaiRui Chemical Co. Ltd.; Hebei City, China), which are polymer resins with sulfonic acid ($SO_3H$) functional groups appended.

An embodiment of the method includes selecting the introduced butene hydration catalyst from the group consisting of a homogeneous butene hydration catalyst, a heterogeneous hydration catalyst, and combinations thereof. Some homogeneous/heterogeneous acid combination systems are known to produce a synergetic effect in regards to conversion efficiency or selectivity, or both, of alkenes to alcohols. In embodiments of the butanol production system containing heterogeneous hydration catalyst in the baffled cells, a embodiment of the butanol production process includes introducing a homogeneous butene hydration catalyst into the internal baffle single pass reactor.

Hydration catalyst introduction occurs either as a pure material or is diluted in a delivery solution. The hydration catalyst can be introduced diluted in water or mixed butenes to enhance dispersion into the process fluid.

Butanol Production Process Products

The primary product is refined mixed butanols. The composition of the refined butanols product is at least 99 vol. % mixed butanols, or 99.5 vol. % mixed butanols, or 99.7 vol. % mixed butanols, or 99.9 vol. % mixed butanols, or even higher purity. An embodiment of the butanol production system includes where the separation system is operable to produce a refined mixed butanols having a purity of at least 99 percent by volume mixed butanols. Dissolved gases, including butenes, butanes and inerts, are minor impurities that can be present in the refined mixed butanols product.

The butanol production system can recover solids from the crude product. Such solids can include catalytically-active hydration catalyst. The butanol production process can recover the hydration catalyst, neutralize it and then dispose of it outside of the butanol production process. External processes can treat or regenerate the recovered hydration catalyst and recycling it for reintroduction into the internal baffle single pass reactor.

The butanol production process selectively separates water from the crude product as part of the refining process. Recovered water can be treated for organics, acid catalysts and solids, and then disposed as a system purge.

The butanol production system can vent gases as part of the separation system. The vent gas acts as a system purge. The vent gas contains inerts and light organic gases, including a small fraction of butenes.

Internal Baffle Single Pass Reactor

The internal baffle single pass reactor is a tubular having an internal fluid conduit defined by an internal wall that is operable to support mixed butene hydration in a pressurized, heated, fluid-filled environment. The tubular has an interior surface or wall partially enclosing a fixed volume between a first end (the proximal or upstream end) and a second end (the distal or downstream end). The operable length of the reactor is the fluid length of the tubular between the proximal end and the distal end. The length of the tubular is much greater than its diameter. The tubular also has an exterior surface or wall along its operating length through which heat transfers between the interior and the exterior.

The internal baffle single pass reactor is operable such that reactants and optionally hydration catalyst can pass into the reactor near the proximal end, mix and form the process fluid. The process fluid traverses the operable length of the reactor from about the proximal end to the distal end along the fluid flow pathway. The crude product passes from the reactor proximate to the distal end.

FIGS. 1-3 show a serpentine-shaped internal baffle single pass reactor; however, the reactor can take any number of physical configurations based upon the use of connected linear and non-linear fluid conduit segments, including standard pipes. One of ordinary skill can envision overall shapes of the internal baffle single pass reactor based upon operational preferences and performance, including temperature control, physical space, maintenance and capital costs.

The primary flow motivator for the process fluid through the internal baffle single pass reactor is the coordinated introduction of reactants and hydration catalyst about the proximate end and the passing of crude product from about the distal end. Although not required, auxiliary flow drivers, including pumps and rotating in-line blades, can provide supplemental momentum to the process fluid.

The internal baffle single pass reactor has at least one reactant feed location near the proximate end of the reactor. The introduction of mixed butenes and water can be as a combined stream or as separate streams. Fresh and recycled mixed butenes and water streams can be comingled or fed separately into the reactor.

The internal baffle single pass reactor has at least one hydration catalyst feed location. The hydration catalyst feed location is downstream from at least one reactant feed location near the proximate end of the internal baffle single pass reactor. This position relative to the reactant feed locations permits the reactants to intermingle with one another before introduction of the hydration catalyst, which facilitates improved selectivity and conversion.

An embodiment of the butanol production system includes multiple reaction zones along the operating length of the internal baffle single pass reactor. In an embodiment, the reaction zone is the operating length between a first mixed butenes introduction location and a second mixed butenes introduction location. In another embodiment, the reaction zone is between a mixed butenes introduction location and the distal end of the reactor. In another embodiment, the reaction zone is the operating length between a first butene hydration catalyst introduction location and a second butene hydration catalyst introduction location. In another embodiment, the reaction zone is between the butene hydration catalyst introduction location and the distal end of the internal baffle single pass reactor. Introducing mixed butenes or butene hydration catalyst through multiple locations along the operating length of the reactor permits a heightened level of process control and butene conversion efficiency. Each reaction zone can have different internal and external process support equipment to facilitate production, including internal baffle structure, manipulation of process fluid flow rate, computer control systems, and reaction zone temperature and pressure manipulation.

At any given point along the operating length of the internal baffle single pass reactor, the internal fluid conduit axis is perpendicular relative to the cross-sectional area of the internal fluid conduit at that point. With no internal additions (for example, internal flow baffles), a fluid would traverse the operating length of the internal baffle single pass reactor and remain generally in alignment with the internal fluid conduit axis while flowing.

Internal Flow Baffles and Baffled Cells

The internal baffle single pass reactor has a series of internal flow baffles along at least a portion of its operating length. An embodiment of the butanol production system includes where the set of internal flow baffles is located along the entire operating length of the internal fluid conduit.

For each internal flow baffle in the internal baffle single pass reactor, the baffle has a side that is directed towards the proximal end of the reactor (the upstream facing side) and an opposite side that is directed towards the distal end of the reactor (the downstream facing side). The baffles are traditionally oriented such that they extend perpendicularly from a location along the internal wall of the reactor and project inward into the internal fluid conduit. Baffles usually are oriented such that they are perpendicular to the internal fluid conduit axis, but other configurations are feasible to one of ordinary skill in the art. The baffles prevent the process fluid from flowing in alignment with the internal fluid conduit axis for the majority of the length of the process fluid flow pathway to encourage heat transfer and mixing.

The internal flow baffles can have a number of physical configurations, including rods, perforated plates, mesh screens, orifice plates (centered and off-centered flow window) and segmented plates. Each baffle has a window edge that at least partially defines the flow window for each baffle. In some baffles, such as an orifice plate, the window edge completely defines the circular void in the baffle through which process fluid flows. In other baffles, the window edge partially defines the void through which the process fluid flows. Upon installation of such a baffle into a reactor, the internal wall of the reactor defines the remainder of the flow window. The flow window's size relative to the size of the baffle, its position relative to the center of the internal fluid conduit and its configuration relative to other adjacent internal baffles (parallel, skewed, perpendicular) are important factors in modifying the direction of travel of the process fluid.

The fluid flow pathway through the interior of the internal baffle single pass reactor is defined by both the internal wall of the reactor and the arrangement of the internal flow baffles, including shape, flow windows, spacing, and orientation of adjacent baffles relative to the internal fluid conduit axis. The length of the process fluid flow pathway is longer than the operating length of the reactor. The baffles increase the distance the process fluid traverses through the reactor because the process fluid must not only flow the distance from the proximal end to the distal end but must also navigate around the internal baffles.

In reactors with multiple reaction zones, different sets of baffles may be present in each reaction zone. The arrangement of internal flow baffles are such that within each set the baffles are arranged in series along the portion of the operating length in which they are located and are spaced equal-distant between each adjacent baffle in the set. An embodiment of the butanol production system includes an internal baffle single pass reactor having more than one set of internal flow baffles along its operating length.

The internal flow baffles along with the internal wall define a set of baffled cells within the internal fluid conduit of the internal baffle single pass reactor. Each baffled cell is bound by the downstream facing side of an upstream baffle and the upstream facing side of the downstream baffle within the set of baffles, and the internal wall of the reactor. The number of baffled cells associated with a set of internal flow baffles is always one less than the number of baffles in the set.

As the process fluid traverses the internal baffle single pass reactor, the process fluid enters a baffled cell through the flow window defined at least in part by the upstream baffle. Upon entering the baffled cell, the process fluid circulates within the cell through both the formation of vortices and the general sinusoidal motion induced in the process fluid by the pushing of the process fluid past the internal flow baffles, mixing reactants, catalyst and product together as well as transferring heat both internally between different portions of the process fluid but also between the process fluid and the internal wall of the reactor. The process fluid then passes from the baffled cell through the flow window defined at least in part by the downstream baffle. The process of traversing baffled cells is repeated as the process fluid passes from baffled cell to baffled cell along the operating length of the reactor.

In an embodiment of the butanol production process the introduction of the butene hydration catalyst is optional. In such processes, the internal baffle single pass reactor contains a solid, heterogeneous butene hydration catalyst to selectively convert the mixed butenes in the process fluid into mixed butanols. Although the catalyst can be contained anywhere within the internal fluid conduit of the reactor, the most effective location for positioning the catalyst to maximize mixing of the reactants and conversion is in each baffled cell.

The position of the solid, heterogeneous butene hydration catalyst within each baffled cell can vary depending on the material, structure and application of the catalyst to the baffled cell components. In the shape of pellets, spheres or other loose and generally unstructured forms, the catalyst can be enveloped in a container or other physical restraining means, including a structured frame with flow holes or slots and a wire mesh bag, that permits process fluid to flow freely into and out from the accumulation of catalyst while not permitting the catalyst to be carried out of the container. This prevents the catalyst from moving with the process fluid flow downstream towards the distal end of the internal baffle single pass reactor and fouling the separations system. The free-form structure of unstructured catalyst can permit their placement directly in the process fluid flow pathway, including the flow window of the internal flow baffles. An embodiment of the butanol production system includes where the heterogeneous butene hydration catalyst is located such that the process fluid flowing through the flow window of the downstream baffle contacts the heterogeneous butene hydration catalyst, and the embodiment of the butanol production process includes where the reaction of the mixed butenes and water occurs in each baffled cell proximate to the downstream flow window. The position of the catalyst can be such that the process fluid flowing through the flow window of the upstream baffle contacts the heterogeneous butene hydration catalyst. Other forms of the catalyst, including structured forms such as lattices, matrix and sheets, and "amorphous" forms such as curable, thermoplastic and other malleable shapes, permit the catalyst to be mounted, adhered, painted or spray-coated onto the inward-facing surfaces of the internal wall and internal flow baffles defining the baffled cell. An embodiment of the butanol production system includes where the catalyst is located on the internal wall that defines the baffled cell, and the embodiment of the butanol production process includes where the reaction of the mixed butenes and water occurs in each baffled cell along the internal wall. For each baffled cell, the downstream facing side of the upstream baffle and the upstream facing side of the downstream facing baffle are directed inward towards the baffled cell. An embodiment of the butanol production system includes where the catalyst is located on the side of the internal flow baffles that is directed inwards towards the baffled cell.

External Motion Driver

The butanol production system includes a device external to the internal baffle single pass reactor that induces unsteadiness in the flow of the process fluid without modifying other operating parameters, including temperature, mass flow rate and pressure, of the butanol production process. Inducing unsteadiness in the flow of the process fluid by transferring motion directly into the process fluid using the external motion driver. The external motion driver can be operated with a reciprocating frequency of 2 to 5 Hertz and a reciprocating amplitude of 20-40 millimeters.

External motion drivers include electrical, electro-mechanical, hydraulic, pneumatic, gas injection, compressed gas, chemical-reaction and any other system or apparatus for imparting or transferring motion into the process fluid.

During the butanol production process, the external motion driver induces unsteadiness the process fluid flow by disrupting the momentum of the fluid as it flows through the internal baffle single pass reactor. The external motion driver acts upon the process fluid in a physical manner as the process fluid traverses from the proximal end to the distal end of the reactor. The external motion driver conveys motion, including oscillating, reciprocating, variable and asynchronous fluid motion, into the process fluid using the portion of the apparatus in contact with the process fluid. The motion of the coupled apparatus within the internal fluid conduit creates unsteadiness in the process fluid flow.

Without the induction of unsteadiness, the butanol production process can maintain "steady state" conditions in the internal baffle single pass reactor. A steady state condition is the condition where fluid properties at any point in the system do not change as compared with time. People of ordinary skill in the art of petroleum, petrochemical and chemical operations understand that "steady state operation" includes some minor process variability from time-to-time but that, in general, operating conditions, feed and production rates do not change significantly.

The application of motion by the external motion driver changes the steady state flow condition to one that is an unsteady by disrupting the fluid momentum of the process fluid flow. The unsteady condition results in a cascading effect that affects other process and production conditions, including heat transfer, reaction efficiency and overall productivity of the system, in response to the destabilization of fluid momentum. The unsteadiness occurs during the moment of introduction of the unsteadying motion and lasts for a period afterwards with diminishing effects as a function of time. With no additional unsteadying interaction and by otherwise maintaining consistent operating conditions, a new steady state condition—one that may be similar to the original steady state—may be achieved. Repeated, periodic or continual application of unsteadying motion directed into the process fluid causes a continuous condition of unsteadiness to exist.

The induced unsteady flow condition of the process fluid modifies the relative motion of the process fluid (for example, accelerated, retarded) compared to a fixed position within the internal baffle single pass reactor. The inducement of the unsteady condition does not affect the overall total volumetric or mass flow per unit time through the reactor as feed introduction and crude product passing affect the overall volumetric or mass flow rates of the process.

Transient formation and dissipation of fluid eddies and counter-flows in the process fluid occur during unsteady flow. Resembling the random directional flow associated with turbulence, the unsteady flow also can occur in low Reynolds number flow regimes typical of laminar-type flow. The unsteady flow of the process fluid encourages mixing, reactions and heat transfer in the baffled cells by causing a portion of the process fluid moving through the internal baffle single pass reactor to flow, only for a transient period, in an unpredictable and non-steady manner.

The external motion driver couples to a device that is operable to impart movement directly into the process fluid. Operation of a piston-like operator causes the process fluid flow to surge and regress while still generally flowing through the internal fluid conduit from proximal to distal end. A diaphragm-like apparatus that is in fluid contact with the process fluid expands and contracts against the incompressible process fluid and directly displaces a similar volume in the internal fluid conduit, which creates the desired process fluid flow instability.

An embodiment of the butanol production system includes an oscillator assembly with an oscillator head that has a reciprocating frequency of 2 to 5 Hertz. In such an embodiment, the exterior motion driver is operable to induce unsteadiness in the process fluid flow by oscillating at a frequency of 2 to 5 Hertz, and in alternate embodiments, the external motion driver oscillates at about 3 Hertz. An embodiment of the butanol production system includes an oscillator assembly with an oscillator head that has a reciprocating amplitude of 20-40 millimeters. In such an embodiment, the exterior motion driver is operable to induce unsteadiness in the process fluid flow by oscillating at a amplitude of 20-40 millimeters., and in alternate embodiments, the external motion driver oscillates with an amplitude of about 30 millimeters.

An embodiment of the butanol production system includes more than one external motion driver, where each external motion driver couples to a device that is operable to impart momentum directly into the process fluid. An embodiment of the butanol production process includes operating a first and a second external motion drivers synchronously. Another embodiment of the butanol production process includes operating a first and a second external motion drivers asynchronously.

Temperature Control System

Temperature control systems convey temperature-modifying fluid to the exterior of the internal baffle single pass reactor to maintain an appropriate temperature for the butene hydration reaction. Examples of temperature control systems useful for maintaining the temperature in the internal baffle single pass reactor include heat exchangers, cooling jackets, and air blowers. Examples of useful temperature-modifying fluids include water, ethylene glycol and air. Forced convection of the temperature-modifying fluid is typical.

Separation System

The butanol production system includes a separations system operable to separate mixed butanols, mixed butenes and water from the crude product.

The butanol production system is operable to selectively separate mixed butenes from the crude product to produce a butene-free crude product and recovered mixed butenes. The recovered mixed butenes is useful for recycling by butanol production system and introduction into the internal baffle single pass reactor as a reactant feed. Recycling of unreacted mixed butenes improves butene process efficiency.

The butanol production system is also operable to selectively separate water from the crude product to produce a water-free crude product. The recovered water is useful for recycling by the butanol production system and introduction into the internal baffle single pass reactor as a reactant feed. The water can also be disposed of as part of a system purge.

An embodiment of the butanol production system is operable to separately selectively separate butene hydration catalyst from the crude product. A cyclone separation system induces a centrifugal force into the crude product that causes heavier liquids and solids to separate from the lighter products. Cyclone separation systems are particularly useful with solid, heterogeneous catalysts as the solids easily separate from the remaining liquids upon application of angular momentum. In-line filtration can also perform a similar task of removing solids from the crude product, allowing the solids to accumulates and slough off under their own weight from the filter surface. Vaporizers can introduce heat into the crude product such that portions of the crude product form a vapor. Evaporators, including thin-film evaporators, can separate the high-temperature boiling products and solids from portions of the crude product that at lower operating pressures can achieve a vapor state. The hydration catalyst and any other solids or very heavy liquids recovered can pass out of the butanol production system for recovery or disposal.

An entraining fluid is useful to selectively extract butanols from the crude product. The crude product includes some amount of water, so a water-immiscible organic compound that is easily separable from water and to which mixed butanols have a ready affinity to as compared to water is useful in performing the extraction. An entrainer fluid having a distillation boiling point that is lower than the mixed butanols at atmospheric pressure also is useful as this makes separating the entrainer from the mixed butanols relatively academic. Examples of useful entrainer fluids include pentane, hexane, hexene, cyclohexane, benzene, toluene, xylenes and mixtures thereof.

Introduction of lean entrainer fluid, which is immiscible with the water in the crude product, causes the crude product to separate into two phases: a butanol-rich organic phase, which includes the entrainer, and a butanol-poor aqueous phase. A butanols extraction column can separate the water phase from the entrainer phase. FIGS. 1A-1B show butanols extraction column 184 producing a water phase that is butanol poor, passing as production water 112, and an entrainer and butanol mixture rich in butanol, which passes to butanols separation column 186. Other refining system processes convert the butanol-rich entrainer fluid into refined mixed butanols and lean entrainer fluid.

A pervaporation membrane can directly separate the mixed butanols from the crude product. A butanol production process including a pervaporation membrane selectively pervaporates the mixed butanols and does not selectively pervaporate water. The pervaporate is a vaporous mixed butanol that can be condensed and distilled to form the refined mixed butanols. The retentate is a liquid comprised mostly of water that contains some mixed butanols. The retentate from this sort of refining system is useful to recycle to not only recapture the desired butanols but also to preserve the water for reuse.

Supporting Equipment

Embodiments include many additional standard components or equipment that enables and makes operable the described apparatus, process, method and system. Examples of such standard equipment known to one of ordinary skill in the art includes heat exchanges, pumps, blowers, reboilers, steam generation, condensate handling, membranes, single and multi-stage compressors, separation and fractionation equipment, valves, switches, controllers and pressure-, temperature-, level- and flow-sensing devices.

Operation, control and performance of portions of or entire steps of a process or method can occur through human interaction, pre-programmed computer control and response systems, or combinations thereof.

Operating the Butanol Production System

The butene hydration catalyst is operable to selectively convert mixed butenes into mixed butanols in the process fluid at the operating conditions of the internal baffle single pass reactor. An embodiment of the butanol production process includes operating the butanol production system such that the temperature of the process fluid in the internal baffle single pass reactor is maintained in a range of from about 80° C. to about 150° C. An embodiment of the butanol production process includes operating the butanol production system such that the temperature of the process fluid in the internal baffle single pass reactor is maintained in a range of from about 100° C. to about 120° C. An embodiment of the butanol production process includes operating the butanol production system such that the pressure of the process fluid in the internal baffle single pass reactor is maintained in a range of from about 5 bars to about 70 bars.

Maintaining the mixed butanols, or some of the components of the mixed butanols, in a liquid or critical fluid state, or a combination of both, can enhance mixing in the internal baffle single pass reactor. An embodiment of the butanol production process includes operating the butanol production system such that the temperature and pressure of the process fluid in the internal baffle single pass reactor is maintained in a range such that the mixed butenes are in a liquid state. An embodiment of the butanol production process includes operating the butanol production system such that the temperature and pressure of the process fluid in the internal baffle single pass reactor is maintained in a range such that the mixed butenes are in a supercritical state.

The improved mixing that occurs within the internal baffle single pass reactor permits a higher throughput of material than with standard fixed volume reactor systems. An embodiment of the butanol production process includes operating the butanol production system such that the residence time of the process fluid in the internal baffle single pass reactor is maintained in a range of from about 0.1 hours to about 0.2 hours. A lower residence time ensures a higher space velocity that minimizes the exposure of 1-butene to temperatures that may cause isomerization into less useful 2-butenes.

EXAMPLES

Examples of specific embodiments facilitate a better understanding of the butanol production system and process. In no way should the Examples limit or define the scope of the invention.

Examples 1-4 and Comparative Examples 1-4

An oscillating baffle reactor (OBR) processes five Example mixtures (1-4). An autoclave reactor processes five Comparative Example mixtures (1-4). Each Example has a 30 millimeter amplitude while the autoclave stirs each Comparative Example composition at a rate of 200 rotations per minute (RPM). Both reactors mix the compositions to form homogeneous mixtures of the immiscible reactants. After 1 hour, each type of reactor stops blending, cools down to room temperature and vents unreacted 1-butene. Analyzing the liquid product for each Example and Comparative Example helps determine the amount of 2-butanol present and conversion efficiency of 1-butene.

Table 1 shows the results of the processing the Example and Comparative Example feed compositions in the OBR and the autoclave reactor under similar processing conditions (that is, temperature, time, feed composition). For all four runs, both the amount in weight percent and the 1-butene conversion molar percentage is higher for the OBR-processed materials than for the autoclave-processed materials.

TABLE 1

Examples 1-4 and Comparative Examples 1-4 runs.

| Conditions | Units | OBR Run | | | | Autoclave Run | | | |
|---|---|---|---|---|---|---|---|---|---|
| | | Example 1 | Example 2 | Example 3 | Example 4 | Comparative Example 1 | Comparative Example 2 | Comparative Example 3 | Comparative Example 4 |
| Hydration catalyst D008 | grams | 10.0 | 7.5 | 5.0 | 2.5 | 5.0 | 3.8 | 2.5 | 1.3 |
| 1-butene introduced | mL | 40.0 | 30.0 | 20.0 | 10.0 | 20.0 | 15.0 | 10.0 | 5.0 |
| H2O introduced | mL | 8.0 | 12.0 | 40.0 | 40.0 | 4.0 | 6.0 | 20.0 | 20.0 |
| Molar ratio H2O:1-butene | — | 1.0 | 2.1 | 10.4 | 20.7 | 1.0 | 2.1 | 10.4 | 20.7 |
| Total volume introduced | mL | 48.0 | 42.0 | 60.0 | 50.0 | 24.0 | 21.0 | 30.0 | 25.0 |
| Sec-butanol of total product weight | wt. % | 93 | 50 | 23 | 10 | 32 | 31 | 12 | 5 |
| 1-butene conversion rate | mol. % | 22 | 24 | 55 | 48 | 8 | 15 | 29 | 24 |

Comparative Example of similar water:1-butene molar value ratio and catalyst:1-butene relative relationship. For example, Example 1 is comparable to Comparative Example 1, Example 2 is comparable to Comparative Example 2, and so on. Table 1 shows the composition of Examples 1-4 and Comparative Examples 1-4. Introduced 1-butene, water and total volume are in milliLiters (mL). Molar ratio is a valueless number.

For processing each Example and Comparative Example, the amount of butene hydration catalyst (D008; KaiRui Chemical Co. Ltd.; Hebei City, China) and water for each Example or Comparative Example is introduced into the designated reactor type (OBR; autoclave). The amount of 1-butene under nitrogen pressure is introduced into the designated reactor type for the respective experiment. Upon sealing a reactor, the reactor heats to operating temperature (100-110° C.). For experiments in the autoclave reactor, a heating jacket maintains operating temperature throughout the experiment. For experiments in the OBR, a hot silicone oil bath maintains the operating temperature. Reaction time occurs in both the autoclave and the OBR for one hour. During processing of the Examples, the OBR reactor mixes the Example compositions at a 3 Hertz (Hz) frequency and As seen in Table 1, all of the OBR experimental runs have a higher 1-butene conversion rate relative to the comparable autoclave example run.

Figure 6:
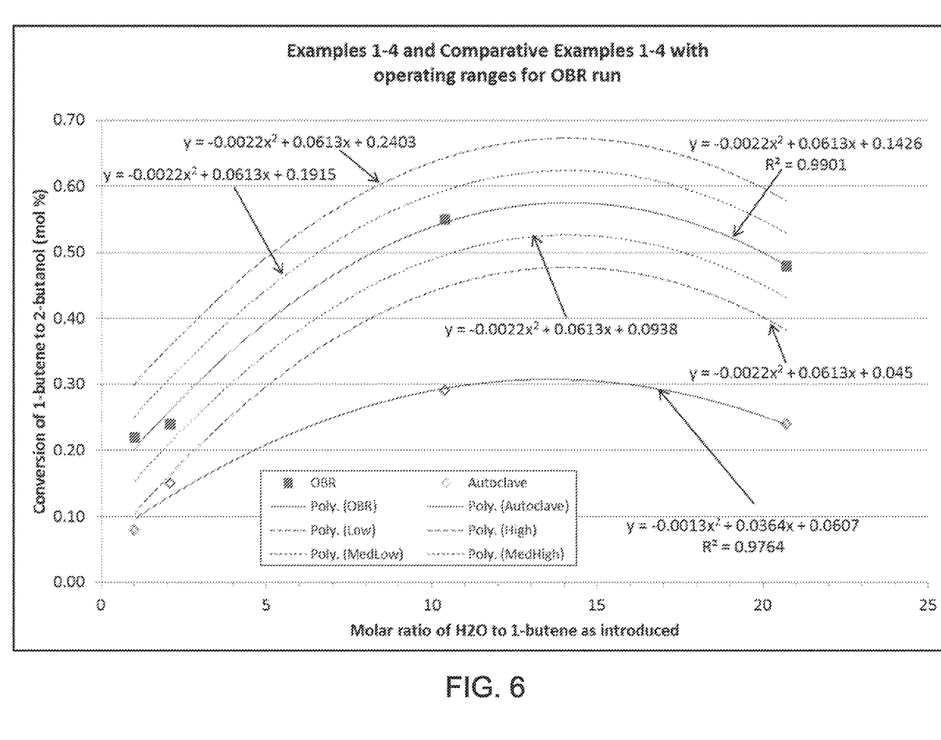
FIG. 6 is a graph showing the mole ratio of introduced water to 1-butene versus conversion of butene to butanol in mole percentage for an oscillating baffle reactor and an autoclave reactor.

FIG. 6 graphically shows mole ratio of water:1-butene introduced versus conversion of butene to butanol in mole percentage for the oscillating baffle reactor (Example) and the autoclave reactor (Comparative Example). FIG. 6 is a plot of the data from Table 3 of molar ratio introduced into the reactor versus the determined 1-butene conversion rate. The data for each set of information (Example and Comparative Example) is curve fit using a second-order polynomial using Microsoft Excel 2010 (Redmond, Wash.).

FIG. 6 also shows the second-order polynomial relationships between molar percent conversion rate of 1-butene with the introduced molar ratio of water:1-butene. For the OBR, the determined second-order relationship is well-fit with a $R^2$ value of greater than 0.99. The second-order polynomial for the OBR experimental runs is given as Equation 1:

$$MCR_{C4=/BtOH} = -0.002173*(MR_{H2O:C4=})^2 + 0.061323*MR_{H2O:C4=} + 0.14264 \quad (\text{Eq. 1}),$$

where $MCR_{C4=/BtOH}$ is the molar conversion rate of 1-butene to butanol in mole percent and $MR_{H2O:C4=}$ is the molar ratio of water to 1-butene in the introduced mixture. Equation 1 is determined for a molar ratio range of from about 1 to about 21.

In addition, the entire molar conversion rate values for the OBR experimental runs (Examples 1-4) fit between two second-order polynomial relationships useful for estimating molar conversion rate of 1-butene into butanol. The two equations, similar to Equation 1, are shown graphically in FIG. 6 as dashed lines "Poly. (Low)" and "Poly. (High)". Equations 2 and 3 envelope the molar conversion rate values of Examples 1-4 for the molar ratio range of the Examples:

$$EMCR_{C4=/BtOH} \geq -0.002173*(MR_{H2O:C4=})^2 + 0.061323*MR_{H2O:C4=}+0.045 \quad \text{(Eq. 2) and}$$

$$EMCR_{C4=/BtOH} \leq -0.002173*(MR_{H2O:C4=})^2 + 0.061323*MR_{H2O:C4=}+0.24028, \quad \text{(Eq. 3)},$$

where $EMCR_{C4=/BtOH}$ is the estimated molar conversion rate of 1-butene to butanol in mole percent and $MR_{H2O:C4=}$ is the molar ratio of water to 1-butene in the introduced mixture, which is in a range of from about 1 to about 21. An embodiment of the butanol production method includes operating the butanol production system such that the molar conversion rate of 1-butene to butanol in mole percent is within the range of estimated molar conversion rate values as determined by Equations 2 and 3. An embodiment of the butanol production method includes operating the butanol production system such that the molar conversion rate of 1-butene to butanol in mole percent is about greater than the estimated molar conversion rate values as determined by Equation 2. In addition, two more equations, similar to Equations 1-3, are shown graphically in FIG. 6 as dashed lines "Poly. (MedLow)" and "Poly. (MedHigh)". Equations 4 and 5 envelope the molar conversion rate values of Examples 1-4 for the molar ratio range of the Examples closer to Equation 1 and in between Equations 2 and 3:

$$EMCR_{C4=/BtOH} \geq -0.002173*(MR_{H2O:C4=})^2 + 0.061323*MR_{H2O:C4=}+0.09382 \quad \text{(Eq. 4) and}$$

$$EMCR_{C4=/BtOH} \leq -0.002173*(MR_{H2O:C4=})^2 + 0.061323*MR_{H2O:C4=}+0.19146, \quad \text{(Eq. 5)},$$

where $EMCR_{C4=/BtOH}$ is the estimated molar conversion rate of 1-butene to butanol in mole percent and $MR_{H2O:C4=}$ is the molar ratio of water to 1-butene in the introduced mixture, which is in a range of from about 1 to about 21. An embodiment of the butanol production method includes operating the butanol production system such that the molar conversion rate of 1-butene to butanol in mole percent is within the range of estimated molar conversion rate values as determined by Equations 4 and 5. An embodiment of the butanol production method includes operating the butanol production system such that the molar conversion rate of 1-butene to butanol in mole percent is about greater than the estimated molar conversion rate values as determined by Equation 4.

Example 5 and Comparative Example 5

The OBR used in Examples 1-4 processes an Example mixture 5. The autoclave reactor used for Comparative Examples 1-4 processes a Comparative Example mixture 5. The Example and Comparative Example have a similar water:1-butene molar value ratio and catalyst:1-butene volume relationship. Table 2 shows the composition of Examples 5 and Comparative Examples 5. Introduced 1-butene, water and total volume are in milliLiters (mL). Molar ratio is a valueless number.

Processing of Example 5 and Comparative Example 5 is similar to the processes for Examples 1-4 and Comparative Example 1-4, respectively, except that the butene hydration catalyst is orthophosphoric acid ($H_3PO_4$) (Sigma-Aldrich Corp.; St. Louis, Mo.).

TABLE 2

Example 5 and Comparative Example 5 runs.

| Conditions | Units | OBR Run Example 5 | Autoclave Run Comparative Example 5 |
|---|---|---|---|
| Hydration catalyst H3PO4 | grams | 5.0 | 2.5 |
| 1-butene introduced | mL | 20.0 | 10.0 |
| H2O introduced | mL | 20.0 | 10.0 |
| Molar ratio H2O:1-butene | — | 5.2 | 5.2 |
| Total volume introduced | mL | 45.0 | 20.0 |
| Sec-butanol of total product weight | wt. % | 15 | 2 |
| 1-butene conversion rate | mol. % | 18 | 2 |

Table 2 shows the results of the processing the Example and Comparative Example compositions in an OBR versus an autoclave reactor under similar processing conditions (that is, temperature, time, composition). For the runs, both the amount in weight percent and the 1-butene conversion molar percentage is higher for the OBR-processed materials than for the autoclave-processed materials. Using an acid-hydration conversion catalyst confirms the superiority of using the OBR for similar processing conditions over the autoclave reactor for hydrating 1-butene.

What is claimed is:

1. A butanol production system for producing refined mixed butanols from water and mixed butenes, the butanol production system comprising:
   an internal baffle single pass reactor having
      an internal fluid conduit defined by an internal wall and an operating length between a proximal end and a distal end, the internal fluid conduit selectively receiving the mixed butenes, the water and a butene hydration catalyst such that a process fluid forms comprising water, mixed butenes and mixed butanols, and selectively mixing the process fluid to form a crude product,
      internal flow baffles located along at least a portion of the operating length of the internal fluid conduit, the internal flow baffles being ring shaped and secured the internal wall, and
      baffled cells located consecutively along the operating length and defined at an outer diameter by the internal wall and at a first end and a second end by the internal flow baffles, wherein one of the internal flow baffles defines both the second end of one of the baffled cells and the first end of an adjacent baffled cell;
   a separation system in fluid communication with the internal baffle single pass reactor, oriented for selectively receiving the crude product and separating the water and the mixed butenes from the crude product such that refined mixed butanols is produced, where the separation system is configured to selectively separate the water and the mixed butenes from the crude product to produce the refined mixed butanols having a purity of at least 99 percent by volume mixed butanols; and an oscillator assembly coupled to the proximal end of the internal baffle single pass reactor, the oscillator assembly having a reciprocating oscillator head selectively movable in a back and forth linear motion, and in communication with the process fluid such that the process fluid undergoes a general sinusoidal movement along the internal baffle single pass reactor.

2. The butanol production system of claim 1, wherein each of the internal flow baffles are formed of a disk shaped plate with an orifice extending through the plate.

3. The butanol production system of claim 2, wherein an outer diameter of the disk shaped plate is fixed to the internal wall.

4. The butanol production system of claim 2, wherein the orifice is sized and positioned through the plate to generate vortices within the process fluid in the baffled cells.

5. The butanol production system of claim 1, wherein an outer diameter of the oscillator head slidingly engages the internal wall.

6. The butanol production system of claim 1, wherein the separation system is in fluid communication with the distal end of the internal fluid conduit.

7. The butanol production system of claim 1, wherein the separation system is in fluid communication with at least one of the baffled cells.

8. The butanol production system of claim 1 where the baffled cells are located along an entire operating length of the internal fluid conduit.

9. The butanol production system of claim 1 where the oscillator head has a reciprocating frequency of 2 to 5 Hertz.

10. The butanol production system of claim 1 where the oscillator head has a reciprocating amplitude of 20-40 millimeters.

11. The butanol production system of claim 1, wherein the oscillator assembly includes an external motion driver mechanically coupled to, and selectively driving, the oscillator head.

12. The butanol production system of claim 11, wherein the oscillator assembly includes an oscillator seal section sealingly engaging the internal baffle single pass reactor and a process fluid oscillator member, the process fluid oscillator member mechanically linking the external motion driver to the oscillator head.

13. A method for producing refined mixed butanols from a combination of water and mixed butenes, the method comprising:
providing an internal baffle single pass reactor having
an internal fluid conduit defined by an internal wall and an operating length between a proximal end and a distal end,
internal flow baffles located along at least a portion of the operating length of the internal fluid conduit, the internal flow baffles being ring shaped and secured the internal wall, and
baffled cells located consecutively along the operating length and defined at an outer diameter by the internal wall and at a first end and a second end by the internal flow baffles, wherein one of the internal flow baffles defines both the second end of one of the baffled cells and a first end of an adjacent baffled cell;
introducing the mixed butenes, the water and a butene hydration catalyst into the internal baffle single pass reactor such that a process fluid forms comprising, mixed butenes, water and mixed butanols and passing the process fluid through the internal baffle single pass reactor;
mixing the process fluid within the internal baffle single pass reactor to form a crude product by inducing a generally sinusoidal movement in the process fluid along the internal baffle single pass reactor with an oscillator assembly that is coupled to the proximal end of the internal baffle single pass reactor, the oscillator assembly having a reciprocating oscillator head selectively movable in a back and forth linear motion; and
separating the water and the mixed butenes from the crude product in a separation system that is in fluid communication with the internal baffle single pass reactor to produce refined mixed butanols; where the separation system selectively produces the refined mixed butanols having a purity of at least 99 percent by volume mixed butanols.

14. The method of claim 13, wherein the step of mixing the process fluid within the internal baffle single pass reactor includes inducing vortices in the process fluid in the baffled cells by pushing the process fluid past the internal flow baffles.

15. The method of claim 13, further comprising transferring the process fluid to the separation system at the distal end of the internal fluid conduit.

16. The method of claim 13, further comprising transferring the process fluid from within at least one of the baffled cells to the separation system.

17. The method of claim 13 further comprising operating the oscillator assembly with a reciprocating frequency of 2 to 5 Hertz.

18. The method of claim 13 further comprising operating the oscillator assembly with a reciprocating amplitude of 20-40 millimeters.

19. The method of claim 13 further comprising driving the oscillator head with an external motion driver that is mechanically coupled to the oscillator head.

20. The method of claim 19 further comprising sealingly engaging the internal baffle single pass reactor and a process fluid oscillator member with an oscillator seal section that mechanically links the external motion driver to the oscillator head.

* * * * *